(12) United States Patent
Griffin, III et al.

(10) Patent No.: US 12,133,785 B2
(45) Date of Patent: Nov. 5, 2024

(54) PROCESS FOR FABRICATING A DIGITAL BITE OPENING APPLIANCE DURING ORTHODONTIC TREATMENT

(71) Applicant: LightForce Orthodontics, Inc, Cambridge, MA (US)

(72) Inventors: Alfred Charles Griffin, III, Lynnfield, MA (US); Dylan Winchell, Canton, MA (US); Alexander Yarmarkovich, Swampscott, MA (US)

(73) Assignee: LightForce Orthodontics, Inc., Burlington, MA (US)

( * ) Notice: Subject to any disclaimer, the term of this patent is extended or adjusted under 35 U.S.C. 154(b) by 0 days.

(21) Appl. No.: 17/025,312

(22) Filed: Sep. 18, 2020

(65) Prior Publication Data

US 2021/0077227 A1  Mar. 18, 2021

Related U.S. Application Data

(60) Provisional application No. 63/048,769, filed on Jul. 7, 2020, provisional application No. 62/902,131, filed on Sep. 18, 2019.

(51) Int. Cl.
*A61C 7/00* (2006.01)
*A61B 6/40* (2024.01)
(Continued)

(52) U.S. Cl.
CPC ............... *A61C 7/10* (2013.01); *A61B 6/4085* (2013.01); *A61B 6/51* (2024.01); *A61C 7/002* (2013.01);
(Continued)

(58) Field of Classification Search
CPC .. A61C 7/002; A61C 7/10; A61C 7/08; A61C 2007/004; A61C 9/0006;
(Continued)

(56) References Cited

U.S. PATENT DOCUMENTS 4,330,277 A * 5/1982 Beu ...................... A61C 19/045
                                                                    433/73
5,724,746 A * 3/1998 Mack ................... A61B 5/1121
                                                                    33/514
(Continued)

FOREIGN PATENT DOCUMENTS

EP           2 949 289 A1     12/2015
WO    WO-2005115266 A2 *   12/2005    .......... A61C 13/0004
WO     WO 2018/045135 A1     3/2018

OTHER PUBLICATIONS

U.S. Appl. No. 18/340,428, filed Jun. 23, 2023, McKay.
(Continued)

*Primary Examiner* — Edward Moran
*Assistant Examiner* — Matthew P Saunders
(74) *Attorney, Agent, or Firm* — Wolf, Greenfield & Sacks, P.C.

(57) ABSTRACT

Embodiments may provide Bite Opening Devices (BODs) that are quicker and easier to place and provide improved accuracy. For example, a method may include using a computer system to perform: receiving data relating to teeth and jaws of a person, identifying a hinge axis of the jaw in three dimensional space using the data relating to teeth and jaws of a person, rotating the jaw to provide a desired clearance of the teeth, placing at least one Bite Opening Device on the teeth so as to provide the desired clearance of the teeth, and generating data defining a bonding tray to fit over the teeth, the bonding tray including a void corresponding to each Bite Opening Device, the generated data defining the bonding tray to be used for manufacturing the bonding tray using additive manufacturing.

19 Claims, 6 Drawing Sheets

(51) Int. Cl.
  *A61B 6/51* (2024.01)
  *A61C 7/10* (2006.01)
  *A61C 9/00* (2006.01)
  *B33Y 50/00* (2015.01)
  *G06F 30/00* (2020.01)
  *G06F 30/12* (2020.01)

(52) U.S. Cl.
  CPC ............ *A61C 9/0006* (2013.01); *B33Y 50/00* (2014.12); *G06F 30/00* (2020.01); *G06F 30/12* (2020.01)

(58) Field of Classification Search
  CPC . A61C 11/00–084; G06F 30/00; G06F 30/12; A61B 6/14; B33Y 50/00
  USPC .................................................. 433/2, 19, 24
  See application file for complete search history.

(56) References Cited

U.S. PATENT DOCUMENTS

| | | | | |
|---|---|---|---|---|
| 6,386,868 B1* | 5/2002 | Fujita | ...................... | A61C 11/08 433/55 |
| 6,464,494 B1* | 10/2002 | Young | ...................... | A61C 7/16 433/18 |
| 6,582,229 B1* | 6/2003 | Miller | ...................... | A61C 11/00 433/213 |
| 7,918,665 B2* | 4/2011 | Kadobayashi | ....... | A61C 13/097 433/197 |
| 8,257,079 B1* | 9/2012 | Plowman | ................ | A61F 5/566 433/18 |
| 8,439,671 B2* | 5/2013 | Cinader, Jr. | ......... | A61C 19/004 433/3 |
| 9,844,424 B2* | 12/2017 | Wu | ........................... | A61C 7/36 |
| 10,299,894 B2* | 5/2019 | Tanugula | ................. | A61C 7/36 |
| 10,548,690 B2* | 2/2020 | Wen | ....................... | G16H 30/20 |
| 2003/0031976 A1* | 2/2003 | Clark | ...................... | A61C 7/00 433/19 |
| 2006/0014117 A1* | 1/2006 | Abels | ...................... | A61C 7/36 433/18 |
| 2006/0223031 A1* | 10/2006 | Cinader | ................. | B33Y 80/00 433/213 |
| 2007/0190481 A1* | 8/2007 | Schmitt | .................. | A61C 19/04 433/68 |
| 2007/0190492 A1* | 8/2007 | Schmitt | ............. | A61C 13/0004 433/213 |
| 2010/0191510 A1* | 7/2010 | Kopelman | ........... | A61C 19/045 703/1 |
| 2015/0238284 A1* | 8/2015 | Wu | ........................ | A61C 7/002 433/19 |
| 2016/0157969 A1* | 6/2016 | Fisker | .................. | A61B 5/0088 703/11 |
| 2018/0078342 A1* | 3/2018 | Gardner | .................... | A61C 7/36 |
| 2019/0125494 A1* | 5/2019 | Li | ........................... | A61C 7/08 |
| 2019/0377327 A1 | 12/2019 | Griffin, III et al. | | |
| 2020/0146781 A1 | 5/2020 | Murrell | | |
| 2020/0146790 A1* | 5/2020 | Marshall | .............. | A61C 9/0053 |
| 2020/0214810 A1* | 7/2020 | Richter | ................ | A61C 9/0053 |
| 2020/0268495 A1* | 8/2020 | Ryakhovsky | .......... | A61C 19/05 |
| 2020/0275996 A1* | 9/2020 | Tong | ....................... | B33Y 80/00 |
| 2021/0401546 A1* | 12/2021 | Gardner | ................. | A61C 7/146 |

OTHER PUBLICATIONS

PCT/US2023/026039, Aug. 23, 2023, Invitation to Pay Additional Fees.
PCT/US2023/026039, Oct. 16, 2023, International Search Report and Written Opinion.
Invitation to Pay Additional Fees mailed Aug. 23, 2023 for International Application No. PCT/US2023/026039.
International Search Report and Written Opinion mailed Oct. 16, 2023 for International Application No. PCT/US2023/026039.

* cited by examiner

PROCESS FOR FABRICATING A DIGITAL BITE OPENING APPLIANCE DURING ORTHODONTIC TREATMENT

CROSS-REFERENCE TO RELATED PATENT APPLICATION(S)

This patent application claims the benefit of U.S. provisional application No. 62/902,131, filed Sep. 18, 2019, and U.S. provisional application No. 63/048,769, filed Jul. 7, 2020, the contents of which are all incorporated in their entirety herein.

BACKGROUND OF THE INVENTION

1. Field of the Invention

An embodiment of present invention relates generally to the manufacturing of a bite-opening device (BOD) which are frequently termed lingual bite blocks, build-ups, buttons, bite ramps, or Bite Turbos.

2. Description of the Related Art

BODs are commonly used in orthodontic practice to keep the mandible (lower jaw) from achieving maximum intercuspation (MIP) or in more familiar terms to "open the bite". Orthodontic practitioners typically require this during treatment to help avoid occlusal interferences with fixed appliances such as brackets and wires, but they may also be used for orthodontic tooth-moving purposes such as in correcting crossbite or intruding certain teeth or segments of teeth, or as an early treatment device to redirect dental development.

With the introduction of digitally planned orthodontic treatment with digitally placed and in-direct bonded braces, occlusal interferences with fixed appliances, such as brackets and wires, can be predicted and avoided by accurately positioned BODs. These BOD's today are typically placed by hand, cured by light and shaped to the desired occlusion by a manual process. As a result, placing current BODs is a long and arduous clinical procedure, and often is inaccurate in its amount of proper bite opening, which is uncomfortable for the patient and/or doesn't have its intended effect.

Accordingly, a need arises for techniques to provide BODs that are quicker and easier to place and provide improved accuracy.

SUMMARY

Embodiments may provide BODs that are quicker and easier to place and provide improved accuracy. With the advent of digital orthodontic appliances such as the 3D printed brackets, embodiments may add BODs to a patient's dentition in precisely the intended shape and at the correct location.

For example, in an embodiment, a method may comprise using a computer system comprising a processor, memory accessible by the processor, and computer program instructions stored in the memory and executable by the processor to perform: receiving data relating to teeth and jaws of a person, identifying a hinge axis of the jaw in three dimensional space using the data relating to teeth and jaws of a person, rotating the jaw to provide a desired clearance of the teeth, placing at least one Bite Opening Device on the teeth so as to provide the desired clearance of the teeth, and generating data defining a bonding tray to fit over the teeth, the bonding tray including a void corresponding to each Bite Opening Device, generated data defining the bonding tray to be used for manufacturing the bonding tray using additive or subtractive manufacturing.

In embodiments, each void may be filled by a bondable dental material to create separation of the dentition for orthodontic purposes. The material left by the void after the bonding process is configured to apply orthodontic vectors of force to the teeth by using masticatory forces. The masticatory forces may center around a hinge axis that approximates physiological rotation, translation or parafunctional activity of a temporomandibular joint. The hinge axis may be identified as being within one of: a 1.0 cm radius of a radiographic landmark portion, a 1.0 cm radius of the temporomandibular joint from a cone-beam CT scan, within a 5 cm radius of upper second molars, or within a 5.0 cm radial sphere with a center 5 cm distal, 4 cm vertical and 1 cm buccal to a DB cusp of the upper second molars. Each void may be filled with a biocompatible pre-formed Bite Opening Device fabricated via either additive or subtractive manufacturing, to be adhesively bonded to a tooth. The method may further comprise manufacturing the bonding tray using additive manufacturing based on the generated data defining the bonding tray. The method may further comprise filling at least one void with a bondable dental material to create separation of the dentition for orthodontic purposes.

In an embodiment, an apparatus may comprise a bonding tray to fit over teeth of a person, the bonding tray including a void corresponding to each Bite Opening Device, the bonding tray manufactured using additive or subtractive manufacturing, the bonding tray manufactured based on generated data defining the bonding tray.

In embodiments, the data defining the bonding tray may be generated using a computer system comprising a processor, memory accessible by the processor, and computer program instructions stored in the memory and executable by the processor to perform: receiving data relating to teeth and jaws of a person, identifying a hinge axis of the jaw in three dimensional space using the data relating to teeth and jaws of a person, rotating the jaw to provide a desired clearance of the teeth, placing at least one Bite Opening Device on the teeth so as to provide the desired clearance of the teeth, and generating the data defining a bonding tray. At least one void may be filled by a bondable dental material to create separation of the dentition for orthodontic purposes. The material left by the void may be configured to apply orthodontic vectors of force to the teeth by using masticatory forces. The masticatory forces may center around a hinge axis that approximates physiological rotation, translation or parafunctional activity of a temporomandibular joint. The hinge axis may be identified as being within one of: a 1.0 cm radius of a radiographic landmark portion, a 1.0 cm radius of the temporomandibular joint from a cone-beam CT scan, within a 5 cm radius of upper second molars, or within a 5.0 cm radial sphere with a center 5 cm distal, 4 cm vertical and 1 cm buccal to a DB cusp of the upper second molars.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION OF THE INVENTION

Embodiments may provide BODs that are quicker and easier to place and provide improved accuracy. With the advent of digital orthodontic appliances such as the 3D printed brackets, embodiments may add BODs to a patient's dentition in precisely the intended shape and at the correct location.

Figure 1:
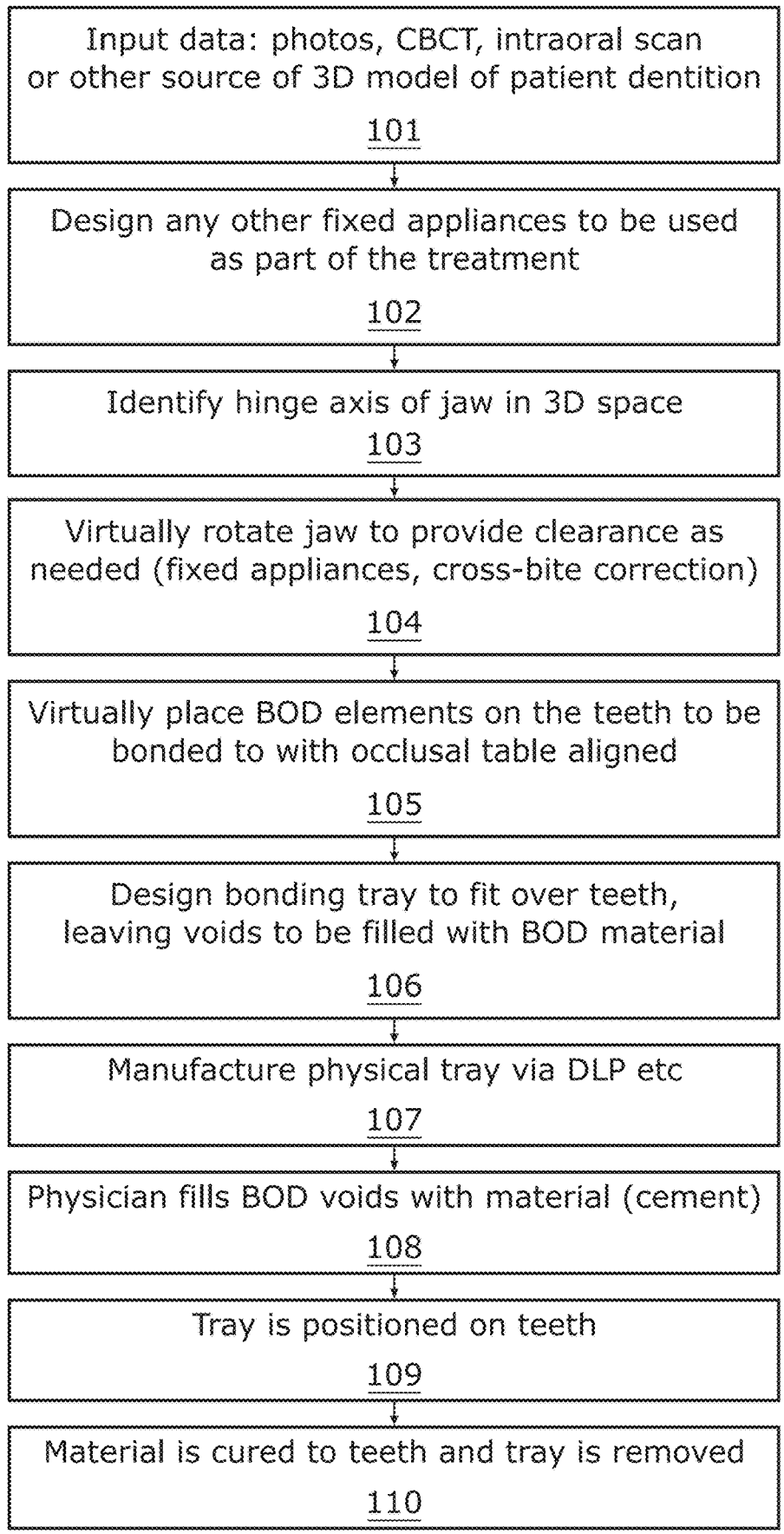
FIG. 1 is an exemplary flow chart of a process for creating custom BOD IDB-type mold-forms.

An exemplary process 100 for creating custom BOD IDB-type mold-forms is shown in FIG. 1. Process 100 begins with 101, in which input data relating to the teeth, mouth, and jaws of a patient may be received, including the relation between the upper and lower jaws such as the amount of overbite and overjet, as well as the class relationship. Such data may include, for example, photos, 3D photometry, CBCT, intraoral scan or other sources of 3D model of patient dentition, such as meshes: such as .stl, .btf, .step, .3DS, .obj, .ply, .stp, .amf, or point-clouds: such as .VTK, .dicom, VDB; or B-rep files: such as .sld, .sldasm, .sldprt, .sld, .prt. At 102 any other fixed orthodontic appliances to be used as part of the treatment may be designed. Such appliances may include, for example, fixed lingual or labial orthodontic braces or clear aligner attachments, or clear aligners.

At 103: the hinge axis of jaw may be identified in 3D space using the input data received at 101, such as 2D images, radiographs or 3D scans, such as from a CB-CT. Typically the hinge axis may be defined as the area in the center, or within a 12 mm radius circle of this point, of the head of the condyle as indicated at 201, shown in FIG. 2. At 104, the lower jaw may be virtually rotated to provide clearance as needed, for example, so as to avoid fixed appliances, making room for cross-bite correction. At 105, the BOD elements may be virtually placed on the teeth to be bonded to, with, for example, the occlusal table parallel, or within 15 degrees of parallel, to the opposing jaw's plane of occlusion and in contact with the directly opposing teeth. At 106, trays may be designed with voids to fit over the teeth, leaving spaces to be filled with BOD material, with a path to take off the tray, while avoiding more than 80 degrees of undercuts in the tray. At 107, physical trays may be manufactured, for example, using a digital manufacturing method, such as additive manufacturing (3D Printing) or subtractive manufacturing (milling).

At 108, the BOD voids in the tray may be filled with material, such as by a Doctor or Doctor's assistant. At 109, the tray may be positioned on the teeth. At 110, the material may be cured as appropriate, via light-cure or self-cure. At 111, the tray may be removed leaving cured or partially-cured BODs attached to the teeth.

Figure 2:
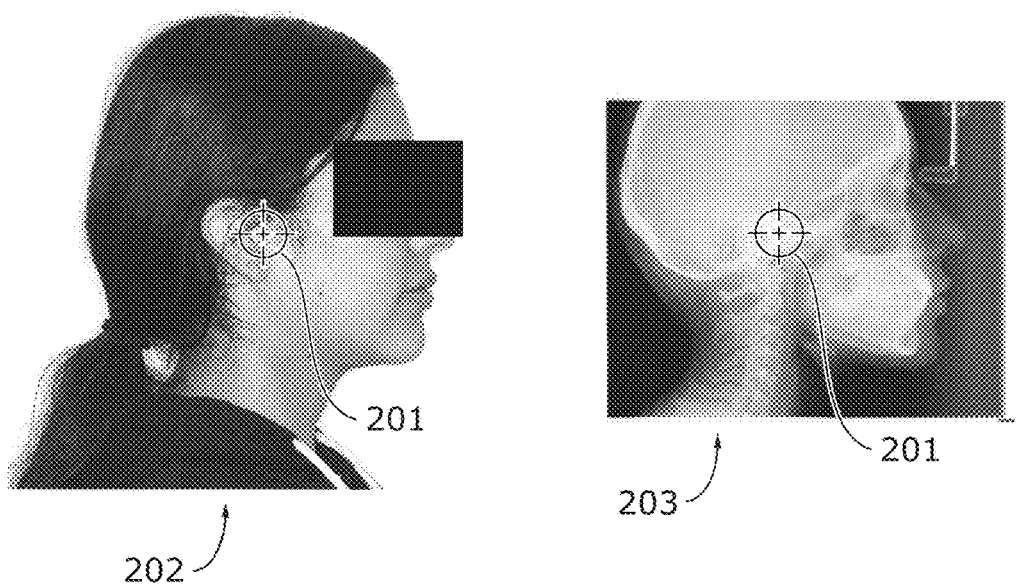
FIG. 2 is an exemplary illustration of a hinge axis of a jaw.

An industry-standard intra oral scan or scanned impression may be taken and used to plan an orthodontic case that will be treated with an orthodontic appliance—most commonly fixed appliances such as stock or customized braces, but BODs may also be used in conjunction with or in place of removable appliances such as with bite plate retainers or clear aligners that create a premature anterior contact and resultant posterior bite opening. The software must then emulate a bite opening arch with reasonable accuracy, for example, a Cone beam computed tomography (CB-CT) scan (DICOM file format or other), a lateral cephalometric radiograph, or a 2D image of the patient's face or 3D digital photometry of a patient's face may be used to approximate the hinge axis 201 of the tempo-mandibular joint (TMJ). This rotational point is then used to approximate the opening and closing of the digital upper and lower dentition in the software, as shown in FIG. 2. FIG. 2 illustrates an example of a hinge axis of a jaw plus types of diagnostic tools used to approximate the hinge angle. Shown in this example are a mandibular hinge axis of rotation 201, an orthodontic profile photo 202, and a lateral cephalometric radiograph 203.

In embodiments, this horizontal hinge axis may only simulate rotational TMJ movement, as no BOD should open the bite enough to require any translational TMJ simulation. A vertical or sagittal axis may also be established to account for excursive movements, especially as used with CB-CT scans. A maximum of, for example, 10 mm of bite opening on the horizontal hinge axis (as measured from the incisal edges of the maxillary and mandibular incisors) may be simulated so as to avoid any translational movements.

Figure 3:
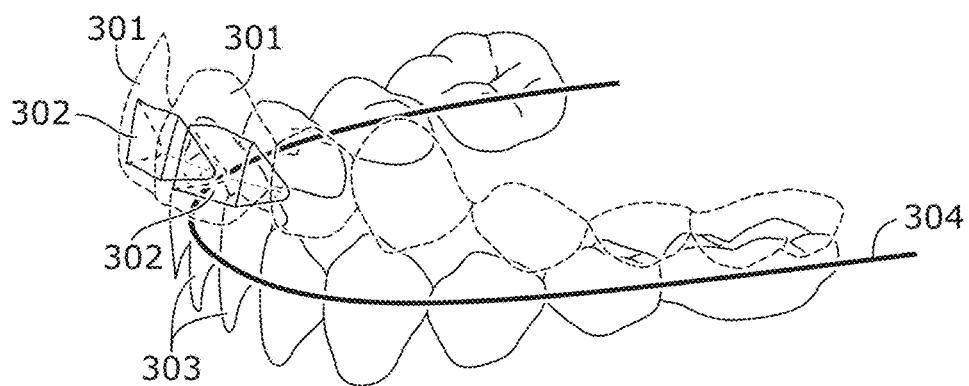
FIG. 3 is an exemplary illustration of an anterior BOD parallel to the occlusal plane.

FIG. 3 illustrates an example of an anterior BOD parallel to an occlusal plane based on a patient's overall treatment plan. Shown in FIG. 3 are maxillary teeth 301 to which the BOD is to be bonded, a plurality of BODs 302, mandibular teeth 303 that will bite on BODs 302, and the occlusal arch/plane 304, where arch plane 304 is defined as the anticipated plane of a wire that would become straight at the case's completion. When the digital orthodontic appliances are placed and the treating dentist determines that the BODs are required, both a BOD shape and BOD position must be determined. BOD shape may look different for an anterior BOD or a posterior BOD depending on the tooth to be bonded, but it must be in contact with enamel. This shape is designed in software as a Boolean subtraction from existing tooth structure such that when a bonding tray is seated on the teeth, there will be a void between the tooth and tray that will be filled by a resin that will become the BOD 302. This bonding tray is designed digitally to allow for accurate physical placement of the BOD and ensure accuracy in bite opening. A key aspect of this accurate physical placement is that each BOD and bonding tray is designed to be patient-specific and follow the structure of the BOD adhered tooth 301 but also the adjacent teeth. The adjacent tooth geometry is used not only to aid in placement accuracy but also in order to give tactile positioning feedback for additional positional accuracy, as well as ensure there is no interference between the BOD and the adjacent teeth. The bonding jig may cover 100% or less of the labial and or lingual surface of the teeth. The coverage is designed however to avoid interference with labial or lingual fixed orthodontic appliances. The bonding tray may also have a flat occlusal shelf to allow for even pressure distribution during application to enhance positional accuracy and avoid rocking of the tray during placement and bonding. The bonding tray may be separated into separate segments to provide easier application, which may be determined based on a calculated path of dram to remove the BOD, and may be designed via 3 dimensional mirroring for staged treatments in the case of unerupted teeth.

Figure 4:
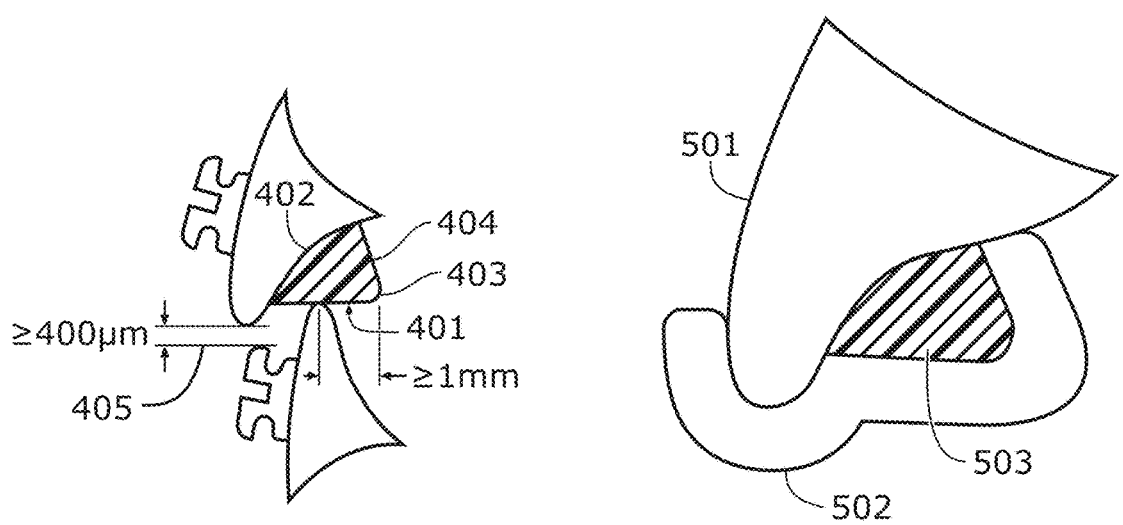
FIG. 4 is an exemplary illustration of an anterior BOD being used to open the bite.

FIG. 4 illustrates an example of an anterior BOD being used to open the bite 405 at least 400 µm from the nearest orthodontic appliance. In this example, the BOD extends ~2 mm past the lower incisor. An anterior BOD may include several key features: 1) an occlusal table 401 meant to be bitten on, which may be +/−15 degrees parallel with the opposing digital arch plane of occlusion 304, shown in FIG. 3; 2) an interface of the BOD with the tooth 402; 3) beveled corners 403 with radius over, for example, 0.20 mm; 4) support wall 404, with an angle less than or equal to 90 degrees from occlusal table 401. This overall shape may be designed to be able to be placed at any vertical (gingival/occlusal) point on the tooth. The length of the occlusal table may protrude, for example, between 0.5 mm to 5 mm from the tooth surface. This occlusal table may be designed to be flat, even, and smooth to avoid bite locking. The BOD may be designed to have a mesial-distal width between, for example, 1 mm and 6 mm in order to be compatible with any tooth structure. An anterior BOD may be applicable to central or lateral incisors as well as canines.

A posterior BOD may also be designed and include similar features, except that the features are not required to be flat as occlusal table 401. A posterior BOD may be applicable to first and second premolars as well as first through third molars. Unlike anterior BODs, these may take many different shapes and may be located on the lingual, labial, or occlusal (palatal cusps) surface of the teeth.

BOD position may be set to the doctor's chosen level, but most frequently will be placed in a position that opens the bite 405 at least 400 µm from the nearest orthodontic appliance, when utilized in conjunction with fixed orthodontic appliances (OA), as shown in FIG. 4.

The software for digital BOD positioning and sizing may compute minimal bite opening, and the minimum, while still functional, occlusal table (as above), which may minimize the patient's discomfort.

Figure 5:
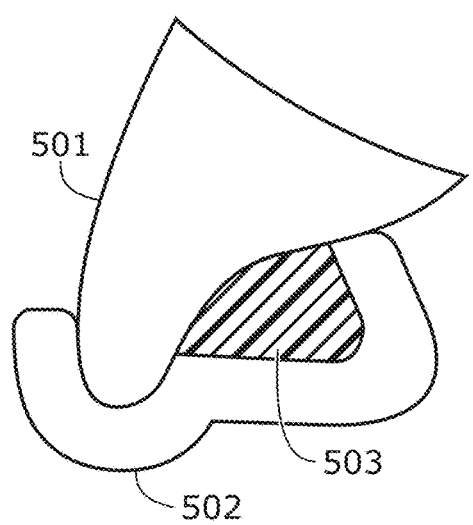
FIG. 5 is an exemplary illustration of an anterior BOD being applied to the tooth with an indirect-bonding mold-form.

FIG. 5 illustrates a custom anterior BOD being applied to a tooth with an indirect-bonding moldform. As shown in this example, a custom tray 502 may be placed over one or more teeth, and in particular, over a tooth 501 to be bonded to. Custom tray 502 may include a void 503. In embodiments, void 503 may be filled with a BOD material, applied to tooth 501 and cured. In embodiments, void 503 contains a pre-formed (bondable) BOD.

BODs may be made of, for example, an Acrylic gel, a compomer paste, a glass ionomer cement, a resin paste, or a flowable resin or another dentally compatible light or self-cure cement. BODs may also be indirectly bonded (via a digitally created tray/jig) pre-formed BOD made via layer manufacturing, additive manufacturing, milling, or any other digital manufacturing method. Pre-formed BODs should have micro or macro mechanical retention via undercuts in the tooth contacting area 402 for bonding via common orthodontic cements.

Figure 6:
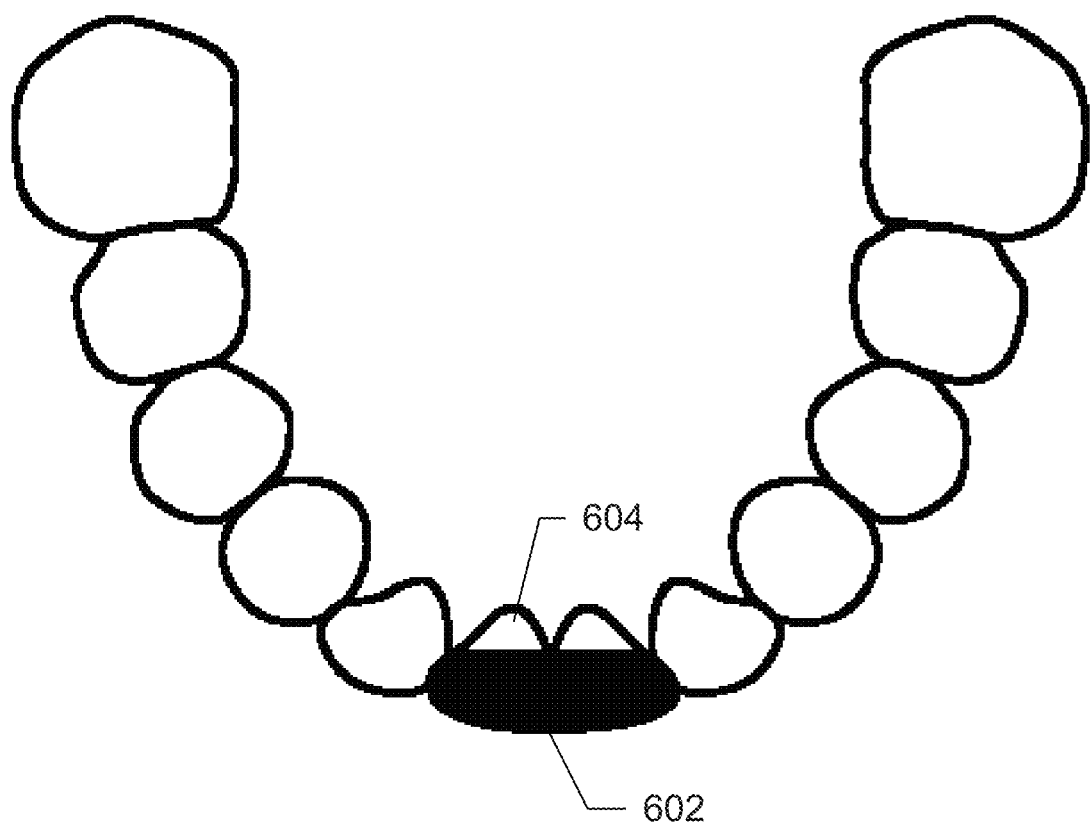
FIG. 6 is an exemplary illustration of a functional turbo bonded to lower incisors for correction of mild anterior crossbite.
Figure 7:
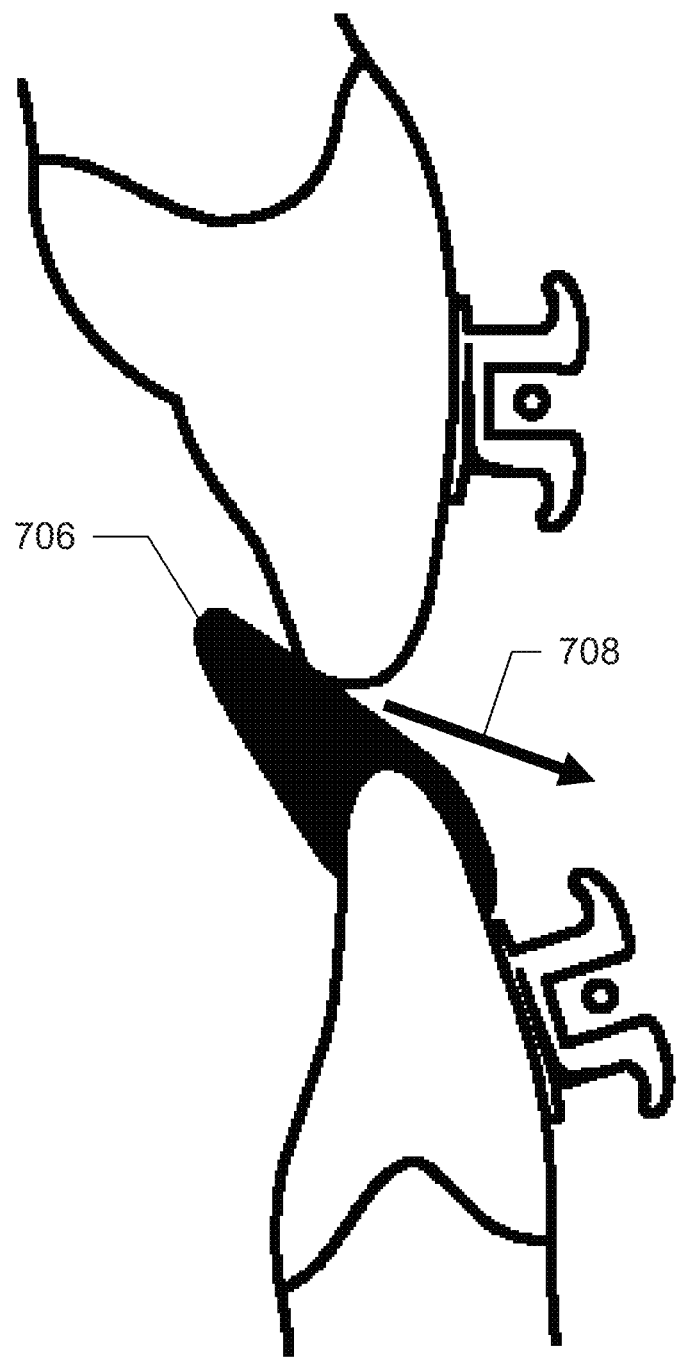
FIG. 7 is an exemplary illustration of a turbo beveled lingually for proper contact with the upper incisor.
Figure 8:
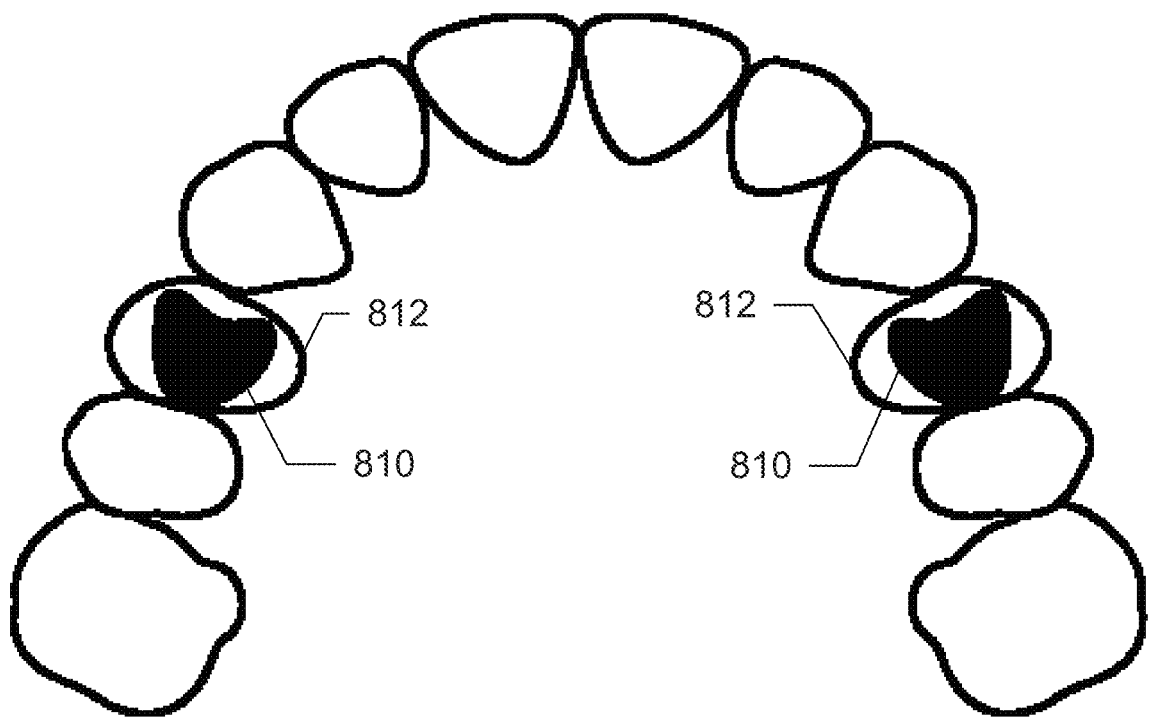
FIG. 8 is an exemplary illustration of functional turbos on first premolars for deep bite correction.
Figure 9:
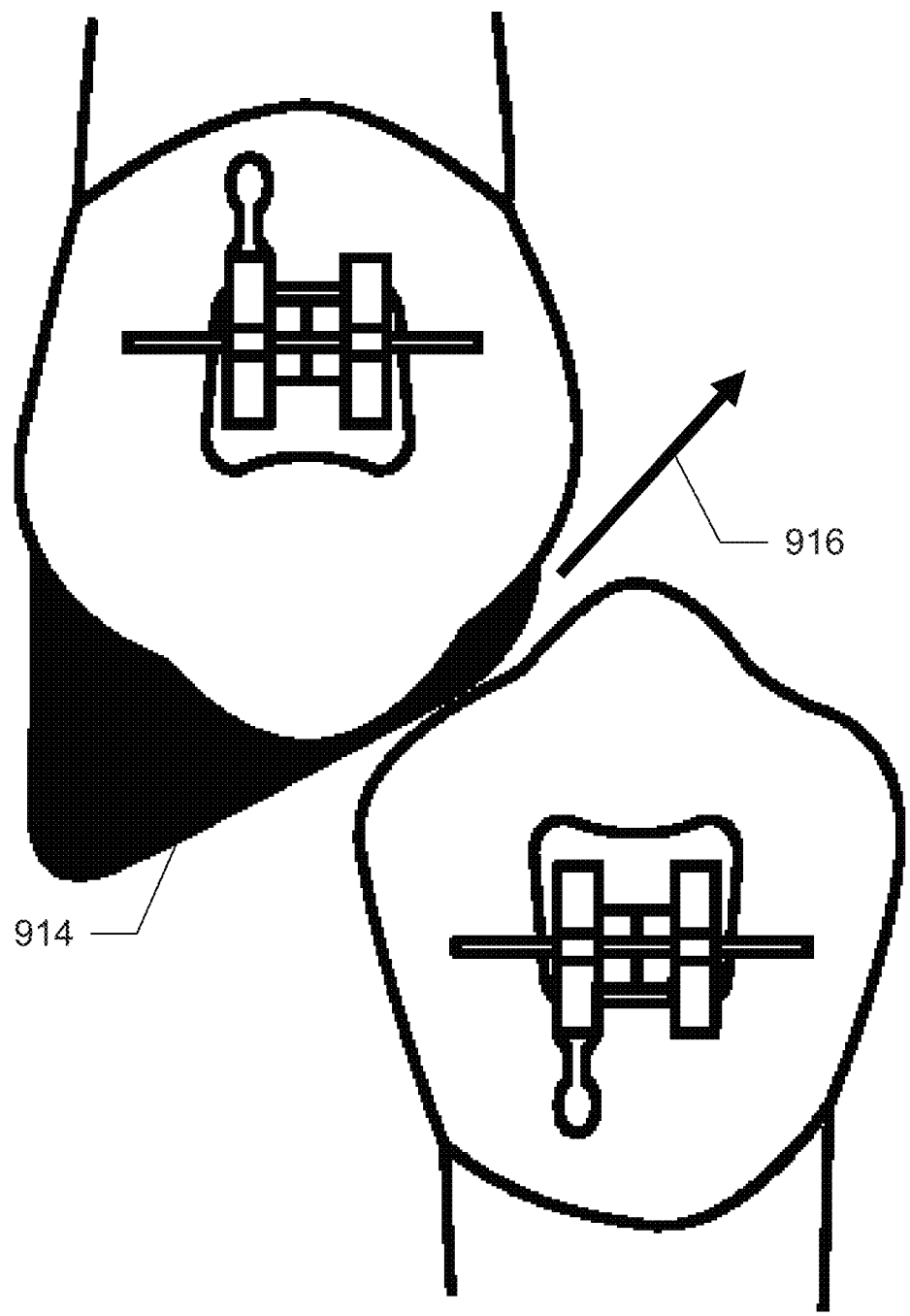
FIG. 9 is an exemplary illustration of turbos to promote disarticulation to help correct Class II malocclusion.

BODs may be used by the treating orthodontic practitioner to protect teeth from occlusal interferences with the orthodontic appliances or to move teeth as functional orthodontic appliances (correcting curve of Spee, intruding/extruding teeth, correct crossbites, preventing palatal impingement of the lower incisors into the palatal tissue, adjusting malocclusions via sagittal correction or acting as a functional class II or class III correcting device, etc.). Functional turbos may take on different shapes to satisfy the intended movement and can be utilized on any tooth, as depicted in FIGS. 6-d, which are exemplary depictions of functional BODs. FIG. 6 depicts a functional BOD 602 bonded to lower incisors 604 for correction of mild anterior crossbite. FIG. 7 depicts BOD 706 beveled lingually 708 for proper contact with upper incisors. FIG. 8 depicts functional BODs 810 on first premolars for correction of deep bite 812. FIG. 9 depicts BOD 914 to promote disarticulation 916 to help correct Class II malocclusion.

What is claimed is:

1. A method comprising:
   using a computer system comprising a processor, memory accessible by the processor, and computer program instructions stored in the memory and executable by the processor to perform:
   receiving three dimensional (3D) model data describing a plurality of teeth, including one or more lower teeth and one or more upper teeth, and a lower jaw of a person;
   virtually placing a 3D model of an orthodontic appliance on a first tooth of the plurality of teeth according to an orthodontic treatment plan for the person;
   identifying a hinge axis of the lower jaw of the person in three dimensional space by approximating the hinge axis using the 3D model data describing the lower jaw;
   virtually positioning the one or more lower teeth relative to the one or more upper teeth using the 3D model data and the virtually placed orthodontic appliance by rotating the lower jaw about the identified hinge axis an amount sufficient to produce a clearance of at least a predetermined amount between the orthodontic appliance virtually placed on the first tooth and a second tooth of the plurality of teeth;
   virtually placing, according to the person's orthodontic treatment plan and 3D model data, a 3D model of at least one Bite Opening Device on one or more teeth of the plurality of teeth so as to set the clearance between the second tooth and the orthodontic appliance as a minimum clearance;
   generating data defining a bonding tray to fit over at least some of the plurality of teeth and the at least one Bite Opening Device based on the virtual placement of the 3D model of the at least one Bite Opening Device on the one or more teeth, the bonding tray including a void corresponding to the virtually placed Bite Opening Device, the generated data defining the bonding tray to be used for manufacturing the bonding tray using additive manufacturing; and
   manufacturing the bonding tray using additive manufacturing based on the generated data defining the bonding tray.

2. The method of claim 1, wherein the void is configured to be filled by a flowable or preformed bondable dental material to create separation of the one or more lower teeth and the one or more upper teeth for orthodontic purposes.

3. The method of claim 2, wherein the void is configured to configure the flowable or preformed bondable dental material to apply orthodontic vectors of force to the teeth by using masticatory forces.

4. The method of claim 3, wherein the masticatory forces center around the hinge axis, which approximates physiological rotation, translation or parafunctional activity of a temporomandibular joint.

5. The method of claim 1, wherein the void is configured to be filled with a biocompatible pre-formed Bite Opening Device fabricated via either additive or subtractive manufacturing, to be adhesively bonded to a tooth.

6. The method of claim 1, further comprising:
filling the void with a bondable dental material to create separation of the one or more lower teeth and one or more upper teeth for orthodontic purposes.

7. The method of claim 6, wherein the void is configured to configure the bondable dental material to apply orthodontic vectors of force to the teeth by using masticatory forces.

8. The method of claim 7, wherein the masticatory forces center around the hinge axis that approximates physiological rotation, translation or parafunctional activity of a temporomandibular joint.

9. The method of claim 1, further comprising:
during manufacturing of the bonding tray, the void is filled with a biocompatible pre-formed Bite Opening Device, to be adhesively bonded to a tooth.

10. The method of claim 1, wherein the clearance of the at least one of the plurality of teeth from the orthodontic appliance that is set as the minimum clearance is 400 µm.

11. The method of claim 1, wherein the 3D model of the at least one Bite Opening Device is virtually placed so that the at least one Bite Opening Device has a bottom surface that is parallel to, or within 15 degrees of parallel to, an occlusal plane of the lower jaw or an upper jaw of the person.

12. The method of claim 1, wherein motion of the lower jaw about the identified hinge axis simulates rotational temporomandibular joint movement, and does not simulate translational temporomandibular joint movement.

13. The method of claim 1, wherein the at least one Bite Opening Device has a mesial-distance width between 1 mm and 6 mm.

14. The method of claim 1, wherein identifying the hinge axis further comprises approximating the hinge axis using data of a face of the person.

15. The method of claim 1, further comprising determining a shape of the at least one Bite Opening Device.

16. The method of claim 15, wherein the shape of the at least one Bite Opening Device is determined based on whether the Bite Opening Device is an anterior Bite Opening Device or a posterior Bite Opening Device.

17. The method of claim 15, wherein determining the shape of the at least one Bite Opening Device further comprises using Boolean subtraction.

18. The method of claim 15, wherein determining the shape of the at least one Bite Opening Device further comprises determining a shape of the second tooth and a shape of at least one tooth adjacent to the second tooth.

19. A method of manufacturing a bonding tray using additive manufacturing based on data defining the bonding tray, wherein the data defining the bonding tray was generated by:

receiving three dimensional (3D) model data describing a plurality of teeth, including one or more lower teeth and one or more upper teeth, and a lower jaw of a person;

virtually placing a 3D model of an orthodontic appliance on a first tooth of the plurality of teeth according to an orthodontic treatment plan for the person;

identifying a hinge axis of the lower jaw of the person in three dimensional space by approximating the hinge axis using the 3D model data describing the lower jaw;

virtually positioning the one or more lower teeth relative to the one or more upper teeth using the 3D model data and the virtually placed orthodontic appliance by rotating the lower jaw about the identified hinge axis an amount sufficient to produce a clearance of at least a predetermined amount between the orthodontic appliance virtually placed on the first tooth and a second tooth of the plurality of teeth;

virtually placing, according to the person's orthodontic treatment plan and 3D model data, a 3D model of at least one Bite Opening Device on one or more teeth of the plurality of teeth so as to set the clearance between the second tooth and the orthodontic appliance as a minimum clearance;

generating data defining the bonding tray to fit over at least some of the plurality of teeth and the at least one Bite Opening Device based on the virtual placement of the 3D model of the at least one Bite Opening Device on the one or more teeth, the bonding tray including a void corresponding to the virtually placed Bite Opening Device, the generated data defining the bonding tray to be used for manufacturing the bonding tray using additive manufacturing; and manufacturing the bonding tray using additive manufacturing based on the generated data defining the bonding tray.

* * * * *